United States Patent [19]
Hawkes

[11] Patent Number: 5,985,630
[45] Date of Patent: Nov. 16, 1999

[54] ASSAY FOR DETECTING INHIBITORS OF AMINOACYL-TRNA SYNTHETASES

[75] Inventor: Timothy Robert Hawkes, Bracknell, United Kingdom

[73] Assignee: Zeneca Limited, United Kingdom

[21] Appl. No.: 08/906,488

[22] Filed: Aug. 5, 1997

Related U.S. Application Data

[63] Continuation of application No. 08/320,473, Oct. 6, 1994, abandoned.

[30] Foreign Application Priority Data

Oct. 6, 1993 [GB] United Kingdom ............... 9320563

[51] Int. Cl.$^6$ ....................................................... C12N 9/99
[52] U.S. Cl. ............................ 435/184; 435/21; 435/69.2
[58] Field of Search ........................................ 435/4, 15, 26, 435/69.2, 184, 21

[56] References Cited

U.S. PATENT DOCUMENTS 4,879,223  11/1989  Miyazawa .................................. 435/68
4,886,749  12/1989  Dombou .................................... 435/89

FOREIGN PATENT DOCUMENTS

94/28139  12/1994  WIPO .

OTHER PUBLICATIONS

Malathi V, An Inhibitor which Interferes with the . . . Biochim Et Biophys Acta 517 (1978) 228–235.

Fersht, Alan R., "Editing Mechanisms in Protein Synthesis. Rejection of Valine by the Isoleucyl–tRNA Synthethase", *Biochemistry*, vol. 16, No. 5, (Mar. 8, 1977), pp. 1025–1030.

Fersht, Alan R., et al., "Enzyme Hyperspecificity, Rejection of Threonine by the Valyl–tRNA Synthethase by Misacylation and Hydrolytic Editing", *Biochemistry*, vol. 15, No. 15 (Jul. 27, 1976), pp. 3342–3346.

Howard, Joy L. et al., "Acetyl–CoA carboxylase: a rapid novel assay procedure used in conjunction with the preparation of enzyme from maize leaves", *FEBS*, vol. 261, No. 2 (1990), pp. 261–264.

Baldwin, Anne Norris, et al., "Transfer Ribonucleic Acid--induced Hydrolysis of Valyladenylate Bound to Isoleucyl Ribonucleic Acid Synthase", *Journal of Biological Chemistry*, vol. 241, No. 4 (1966), pp. 839–845.

Lanzetta, Peter A., Alvarez, Lawrence J., Reinach, Peter S., and Candia, Oscar A., "An Improved Assay for Nanomole Amounts of Inorganic Phosphate", Analytical Biochemistry, vol. 100, No. 1, Nov. 15, 1979, pp. 95–97.

Yanagisawa, Tatsuo, Lee, Judy T., Wu, Henry C., and Kawakami, Makoto, Relationship of Protein Structure of Isoleucyl–tRNA Synthetase with Pseudomonic Acid Resistance of *Escherichia coli,* Journal of Biological Chemistry, vol. 269, No. 39, pp. 24304–24309.

Freist, Wolfgang and Sternbach, Hans, "Isoleucyl–tRNA Synthethase from Bakers' Yeast: Variable Discrimination between tRNA and tRNA and Different Pathways of Cognate and Noncognate Aminoacylation under Standard Conditions, in the Presence of Pyrophosphatase, Elongation Factor Tu–GTP Complex, and Spermine", Biochemistry, 1984, 23, pp. 5742–5752.

*Primary Examiner*—Ralph Gitomer
*Attorney, Agent, or Firm*—Marian T. Thomson

[57] ABSTRACT

An assay for detecting inhibitors of amino acyl-tRNA synthetases by incubating a divalent metal cation, ATP, tRNA, a non-cognate amino acid, inorganic pyrophosphatase and aminoacyl-tRNA synthetase, which aminoacyl-tRNA synthetase is in at least a partially pure form, both with and without a potential inhibitor, converting the resulting pyrophosphate to phosphate, detecting phosphate production, and comparing the phosphate production results obtained.

7 Claims, No Drawings

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
       (A) LENGTH: 2820 base pairs
       (B) TYPE: nucleic acid
       (C) STRANDEDNESS: single
       (D) TOPOLOGY: linear (ii) MOLECULE TYPE: cDNA (ix) FEATURE:
       (A) NAME/KEY: CDS
       (B) LOCATION: 1..2814

(xi) SEQUENCE DESCRIPTION: SEQ ID NO:1:

```
ATG AGT GAC TAT AAA TCA ACC CTG AAT TTG CCG GAA ACA GGG TTC CCG       48
Met Ser Asp Tyr Lys Ser Thr Leu Asn Leu Pro Glu Thr Gly Phe Pro
 1               5                  10                  15

ATG CGT GGC GAT CTC GCC AAG CGC GAA CCC GGA ATG CTG GCG CGT TGG       96
Met Arg Gly Asp Leu Ala Lys Arg Glu Pro Gly Met Leu Ala Arg Trp
             20                  25                  30

ACT GAT GAT GAT CTG TAC GGC ATC ATC CGT GCG GCT AAA AAA GGC AAA      144
Thr Asp Asp Asp Leu Tyr Gly Ile Ile Arg Ala Ala Lys Lys Gly Lys
         35                  40                  45

AAA ACC TTC ATT CTG CAT GAT GGC CCT CCT TAT GCG AAT GGC AGC ATT      192
Lys Thr Phe Ile Leu His Asp Gly Pro Pro Tyr Ala Asn Gly Ser Ile
     50                  55                  60

CAT ATT GGT CAC TCG GTT AAC AAG ATT CTG AAA GAC ATT ATC GTG AAG      240
His Ile Gly His Ser Val Asn Lys Ile Leu Lys Asp Ile Ile Val Lys
 65                  70                  75                  80

TCC AAA GGG CTT TCC GGT TAT GAC TCG CCG TAT GTG CCT GGC TGG GAC      288
Ser Lys Gly Leu Ser Gly Tyr Asp Ser Pro Tyr Val Pro Gly Trp Asp
                 85                  90                  95

TGC CAC GGT CTG CCG ATC GAG CTG AAA GTC GAG CAA GAA TAC GGT AAG      336
Cys His Gly Leu Pro Ile Glu Leu Lys Val Glu Gln Glu Tyr Gly Lys
            100                 105                 110

CCG GGT GAG AAA TTC ACC GCC GCC GAG TTC CGC GCC AAG TGC CGC GAA      384
Pro Gly Glu Lys Phe Thr Ala Ala Glu Phe Arg Ala Lys Cys Arg Glu
        115                 120                 125

TAC GCG GCG ACC CAG GTT GAC GGT CAA CGC AAA GAC TTT ATC CGT CTG      432
Tyr Ala Ala Thr Gln Val Asp Gly Gln Arg Lys Asp Phe Ile Arg Leu
    130                 135                 140

GGC GTG CTG GGC GAC TGG TCG CAC CCG TAC CTG ACC ATG GAC TTC AAA      480
Gly Val Leu Gly Asp Trp Ser His Pro Tyr Leu Thr Met Asp Phe Lys
145                 150                 155                 160

ACT GAA GCC AAC ATC ATC CGC GCG CTG GGC AAA ATC ATC GGC AAC GGT      528
Thr Glu Ala Asn Ile Ile Arg Ala Leu Gly Lys Ile Ile Gly Asn Gly
                165                 170                 175

CAC CTG CAC AAA GGC GCG AAG CCA GTT CAC TGG TGC GTT GAC TGC CGT      576
His Leu His Lys Gly Ala Lys Pro Val His Trp Cys Val Asp Cys Arg
            180                 185                 190

TCT GCG CTG GCG GAA GCG GAA GTT GAG TAT TAC GAC AAA ACT TCT CCG      624
Ser Ala Leu Ala Glu Ala Glu Val Glu Tyr Tyr Asp Lys Thr Ser Pro
        195                 200                 205

TCC ATC GAC GTT GCT TTC CAG GCA GTC GAT CAG GAT GCA CTG AAA GCA      672
Ser Ile Asp Val Ala Phe Gln Ala Val Asp Gln Asp Ala Leu Lys Ala
    210                 215                 220
```

-continued

```
AAA TTT GCC GTA AGC AAC GTT AAC GGC CCA ATC TCG CTG GTA ATC TGG      720
Lys Phe Ala Val Ser Asn Val Asn Gly Pro Ile Ser Leu Val Ile Trp
225             230                 235                 240

ACC ACC CGC CGT GGA CTC TGC CTG CCA ACC GCG CAA TCT CTA TTG CAC      768
Thr Thr Arg Arg Gly Leu Cys Leu Pro Thr Ala Gln Ser Leu Leu His
            245                 250                 255

CAG ATT TCG ACT ATG CGC TGG TGC CAG ATC GAC GGT CAG GCC GTG ATT      816
Gln Ile Ser Thr Met Arg Trp Cys Gln Ile Asp Gly Gln Ala Val Ile
                260                 265                 270

CTG GCG AAA GAT CTG GTT GAA AGC GTA ATG CAG CGT ATC GGC GTG ACC      864
Leu Ala Lys Asp Leu Val Glu Ser Val Met Gln Arg Ile Gly Val Thr
                275                 280                 285

GAT TAC ACC ATT CTC GGC ACG GTA AAA GGT GCG GAT GTC GAG CTG CTG      912
Asp Tyr Thr Ile Leu Gly Thr Val Lys Gly Ala Asp Val Glu Leu Leu
        290                 295                 300

CGC TTT ACC CAT CCG TTT ATG GGC TTC GAC GTT CCG GCA ATC CTC GGC      960
Arg Phe Thr His Pro Phe Met Gly Phe Asp Val Pro Ala Ile Leu Gly
305                 310                 315                 320

GAT CAC GTT ACC CTG GAT GCG GGT ACC GGT GCC GTT CAC ACC GCG CCT     1008
Asp His Val Thr Leu Asp Ala Gly Thr Gly Ala Val His Thr Ala Pro
                325                 330                 335

GGC CAC GGC CCG GAC GAC TAT GTG ATC GGT CAG AAA TAC GGC CTG GAA     1056
Gly His Gly Pro Asp Asp Tyr Val Ile Gly Gln Lys Tyr Gly Leu Glu
                340                 345                 350

ACC GCT AAC CCG GTT GGC CCG GAC GGC ACT TAT CTG CCG GGC ACT TAT     1104
Thr Ala Asn Pro Val Gly Pro Asp Gly Thr Tyr Leu Pro Gly Thr Tyr
            355                 360                 365

CCG ACG TTG GAT GGC GTG AAC GTC TTC AAA GCG AAC GAC ATC GTC GTT     1152
Pro Thr Leu Asp Gly Val Asn Val Phe Lys Ala Asn Asp Ile Val Val
370                 375                 380

GCG CTG CTG CAG GAA AAA GGC GCT CTG CTG CAC GTT GAG AAA ATG CAG     1200
Ala Leu Leu Gln Glu Lys Gly Ala Leu Leu His Val Glu Lys Met Gln
385                 390                 395                 400

CAC AGC TAT CCG TGC TGC TGG CGT CAC AAA ACG CCG ATC ATC TTC CGC     1248
His Ser Tyr Pro Cys Cys Trp Arg His Lys Thr Pro Ile Ile Phe Arg
                405                 410                 415

GCG ACG CCG CAG TGG TTC GTC AGC ATG GAT CAG AAA GGT CTG CGT GCG     1296
Ala Thr Pro Gln Trp Phe Val Ser Met Asp Gln Lys Gly Leu Arg Ala
                420                 425                 430

CAG TCA CTG AAA GAG ATC AAA GGC GTG CAG TGG ATC CCG GAC TGG GGC     1344
Gln Ser Leu Lys Glu Ile Lys Gly Val Gln Trp Ile Pro Asp Trp Gly
            435                 440                 445

CAG GCG CGT ATC GAG TCG ATG GTT GCT AAC CGT CCT GAC TGG TGT ATC     1392
Gln Ala Arg Ile Glu Ser Met Val Ala Asn Arg Pro Asp Trp Cys Ile
450                 455                 460

TCC CGT CAG CGC ACC TGG GGT GTA CCG ATG TCA CTG TTC GTG CAC AAA     1440
Ser Arg Gln Arg Thr Trp Gly Val Pro Met Ser Leu Phe Val His Lys
465                 470                 475                 480

GAC ACG GAA GAA CTG CAT CCG CGT ACC CTT GAA CTG ATG GAA GAA GTG     1488
Asp Thr Glu Glu Leu His Pro Arg Thr Leu Glu Leu Met Glu Glu Val
                485                 490                 495

GCA AAA CGC GTT GAA GTC GAT GGC ATC CAG GCG TGG TGG GAT CTC GAT     1536
Ala Lys Arg Val Glu Val Asp Gly Ile Gln Ala Trp Trp Asp Leu Asp
                500                 505                 510

GCG AAA GAG ATC CTC GGC GAC GAA GCT GAT CAG TAC GTG AAA GTG CCG     1584
Ala Lys Glu Ile Leu Gly Asp Glu Ala Asp Gln Tyr Val Lys Val Pro
                515                 520                 525

GAC ACA TTG GAT GTA TGG TTT GAC TCC GGA TCT ACC CAC TCT TCT GTT     1632
Asp Thr Leu Asp Val Trp Phe Asp Ser Gly Ser Thr His Ser Ser Val
            530                 535                 540
```

```
GTT GAC GTG CGT CCG GAA TTT GCC GGT CAC GCA GCG GAC ATG TAT CTG    1680
Val Asp Val Arg Pro Glu Phe Ala Gly His Ala Ala Asp Met Tyr Leu
545                 550                 555                 560

GAA GGT TCT GAC CAA CAC CGC GGC TGG TTC ATG TCT TCC CTA ATG ATC    1728
Glu Gly Ser Asp Gln His Arg Gly Trp Phe Met Ser Ser Leu Met Ile
                565                 570                 575

TCC ACC GCG ATG AAG GGT AAA GCG CCG TAT CGT CAG GTA CTG ACC CAC    1776
Ser Thr Ala Met Lys Gly Lys Ala Pro Tyr Arg Gln Val Leu Thr His
            580                 585                 590

GGC TTT ACC GTG GAT GGT CAG GGC CGC AAG ATG TCT AAA TCC ATC GGC    1824
Gly Phe Thr Val Asp Gly Gln Gly Arg Lys Met Ser Lys Ser Ile Gly
        595                 600                 605

AAT ACC GTT TCG CCG CAG GAT GTG ATG AAC AAA CTG GGC GCG GAT ATT    1872
Asn Thr Val Ser Pro Gln Asp Val Met Asn Lys Leu Gly Ala Asp Ile
610                 615                 620

CTG CGT CTG TGG GTG GCA TCA ACC GAC TAC ACC GGT GAA ATG GCC GTT    1920
Leu Arg Leu Trp Val Ala Ser Thr Asp Tyr Thr Gly Glu Met Ala Val
625                 630                 635                 640

TCT GAC GAG ATC CTG AAA CGT GCT GCC GAT AGC TAT CGT CGT ATC CGT    1968
Ser Asp Glu Ile Leu Lys Arg Ala Ala Asp Ser Tyr Arg Arg Ile Arg
                645                 650                 655

AAC ACC GCG CGC TTC CTG CTG GCA AAC CTG AAC GGT TTT GAT CCA GCA    2016
Asn Thr Ala Arg Phe Leu Leu Ala Asn Leu Asn Gly Phe Asp Pro Ala
            660                 665                 670

AAA GAT ATG GTG AAA CCG GAA GAG ATG GTG GTA CTG GAT CGC TGG GCC    2064
Lys Asp Met Val Lys Pro Glu Glu Met Val Val Leu Asp Arg Trp Ala
        675                 680                 685

GTA GGT TGT GCG AAA GCG GCA CAG GAA GAC ATC CTC AAG GCG TAC GAA    2112
Val Gly Cys Ala Lys Ala Ala Gln Glu Asp Ile Leu Lys Ala Tyr Glu
690                 695                 700

GCA TAC GAT TTT CAC GAA GTG GTA CAG CGT CTG ATG CGC TTC TGC TCC    2160
Ala Tyr Asp Phe His Glu Val Val Gln Arg Leu Met Arg Phe Cys Ser
705                 710                 715                 720

GTT GAG ATG GTT TCC TTC TAC CTC GAC ATC ATC AAA GAC CGT CAG TAC    2208
Val Glu Met Val Ser Phe Tyr Leu Asp Ile Ile Lys Asp Arg Gln Tyr
                725                 730                 735

ACC CCA AAG CGG ACA GTG TGG GCG CGT CGT AGC TGC CAG ACT GCG CTA    2256
Thr Pro Lys Arg Thr Val Trp Ala Arg Arg Ser Cys Gln Thr Ala Leu
            740                 745                 750

TAT CAC ATC GCA GAA GCG CTG GTG CGC TGG ATG GCA CCA ATC CTC TCC    2304
Tyr His Ile Ala Glu Ala Leu Val Arg Trp Met Ala Pro Ile Leu Ser
        755                 760                 765

TTC ACC GCT GAT GAA GTG TGG GGC TAC CTG CCG GGC GAA CGT GAA AAA    2352
Phe Thr Ala Asp Glu Val Trp Gly Tyr Leu Pro Gly Glu Arg Glu Lys
770                 775                 780

TAC GTC TTC ACC GGT GAG TGG TAC GAA GGC CTG TTT GGC CTG GCA GAC    2400
Tyr Val Phe Thr Gly Glu Trp Tyr Glu Gly Leu Phe Gly Leu Ala Asp
785                 790                 795                 800

AGT GAA GCG ATG AAC GAT GCG TTC TGG GAC GAG CTG TTG AAA GTG CGT    2448
Ser Glu Ala Met Asn Asp Ala Phe Trp Asp Glu Leu Leu Lys Val Arg
                805                 810                 815

GGC GAA GTG AAC AAA GTC ATT GAG CAA GCG CGT GCC GAC AAG AAA GTG    2496
Gly Glu Val Asn Lys Val Ile Glu Gln Ala Arg Ala Asp Lys Lys Val
            820                 825                 830

GGT GGC TCG CTG GAA GCG GCG GTA ACC TTG TAT GCA GAA CCG GAA CTG    2544
Gly Gly Ser Leu Glu Ala Ala Val Thr Leu Tyr Ala Glu Pro Glu Leu
        835                 840                 845

TCG GCG AAA CTG ACC GCG CTG GGC GAT GAA TTA CGA TTT GTC CTG TTG    2592
Ser Ala Lys Leu Thr Ala Leu Gly Asp Glu Leu Arg Phe Val Leu Leu
850                 855                 860
```

```
ACC TCC CGC CGC TAC GTT GCA GAC TAT AAC GAC GCA CCT GCT GAT GCt    2640
Thr Ser Arg Arg Tyr Val Ala Asp Tyr Asn Asp Ala Pro Ala Asp Ala
865                 870                 875                 880

CAG CAG AGC GAA GTA CTC AAA GGG CTG AAA GTC GCG TTG AGT AAA GCC    2688
Gln Gln Ser Glu Val Leu Lys Gly Leu Lys Val Ala Leu Ser Lys Ala
                885                 890                 895

GAA GGT GAG AAG TGC CCA CGC TGC TGG CAC TAC ACC CAG GAT GTC GGC    2736
Glu Gly Glu Lys Cys Pro Arg Cys Trp His Tyr Thr Gln Asp Val Gly
            900                 905                 910

AAG GTG GCG GAA CAC GCA GAA ATC TGC GGC CGC TGT GTC AGC AAC GTC    2784
Lys Val Ala Glu His Ala Glu Ile Cys Gly Arg Cys Val Ser Asn Val
        915                 920                 925

GCC GGT GAC GGT GAA AAA CGT AAG TTT GCC TGATGA                      2820
Ala Gly Asp Gly Glu Lys Arg Lys Phe Ala
    930                 935
```

(2) INFORMATION FOR SEQ ID NO:2:

(i) SEQUENCE CHARACTERISTICS:
        (A) LENGTH: 938 amino acids
        (B) TYPE: amino acid
        (D) TOPOLOGY: linear (ii) MOLECULE TYPE: protein (xi) SEQUENCE DESCRIPTION: SEQ ID NO:2:

```
Met Ser Asp Tyr Lys Ser Thr Leu Asn Leu Pro Glu Thr Gly Phe Pro
1               5                   10                  15

Met Arg Gly Asp Leu Ala Lys Arg Glu Pro Gly Met Leu Ala Arg Trp
            20                  25                  30

Thr Asp Asp Leu Tyr Gly Ile Ile Arg Ala Ala Lys Lys Gly Lys
        35                  40                  45

Lys Thr Phe Ile Leu His Asp Gly Pro Pro Tyr Ala Asn Gly Ser Ile
    50                  55                  60

His Ile Gly His Ser Val Asn Lys Ile Leu Lys Asp Ile Val Lys
65                  70                  75                  80

Ser Lys Gly Leu Ser Gly Tyr Asp Ser Pro Tyr Val Pro Gly Trp Asp
                85                  90                  95

Cys His Gly Leu Pro Ile Glu Leu Lys Val Glu Gln Glu Tyr Gly Lys
            100                 105                 110

Pro Gly Glu Lys Phe Thr Ala Ala Glu Phe Arg Ala Lys Cys Arg Glu
        115                 120                 125

Tyr Ala Ala Thr Gln Val Asp Gly Gln Arg Lys Asp Phe Ile Arg Leu
    130                 135                 140

Gly Val Leu Gly Asp Trp Ser His Pro Tyr Leu Thr Met Asp Phe Lys
145                 150                 155                 160

Thr Glu Ala Asn Ile Ile Arg Ala Leu Gly Lys Ile Ile Gly Asn Gly
                165                 170                 175

His Leu His Lys Gly Ala Lys Pro Val His Trp Cys Val Asp Cys Arg
            180                 185                 190

Ser Ala Leu Ala Glu Ala Glu Val Glu Tyr Tyr Asp Lys Thr Ser Pro
        195                 200                 205

Ser Ile Asp Val Ala Phe Gln Ala Val Asp Gln Asp Ala Leu Lys Ala
    210                 215                 220

Lys Phe Ala Val Ser Asn Val Asn Gly Pro Ile Ser Leu Val Ile Trp
225                 230                 235                 240

Thr Thr Arg Arg Gly Leu Cys Leu Pro Thr Ala Gln Ser Leu Leu His
                245                 250                 255
```

-continued

```
Gln Ile Ser Thr Met Arg Trp Cys Gln Ile Asp Gly Gln Ala Val Ile
            260                 265                 270

Leu Ala Lys Asp Leu Val Glu Ser Val Met Gln Arg Ile Gly Val Thr
        275                 280                 285

Asp Tyr Thr Ile Leu Gly Thr Val Lys Gly Ala Asp Val Glu Leu Leu
290                 295                 300

Arg Phe Thr His Pro Phe Met Gly Phe Asp Val Pro Ala Ile Leu Gly
305                 310                 315                 320

Asp His Val Thr Leu Asp Ala Gly Thr Gly Ala Val His Thr Ala Pro
                325                 330                 335

Gly His Gly Pro Asp Asp Tyr Val Ile Gly Gln Lys Tyr Gly Leu Glu
            340                 345                 350

Thr Ala Asn Pro Val Gly Pro Asp Gly Thr Tyr Leu Pro Gly Thr Tyr
        355                 360                 365

Pro Thr Leu Asp Gly Val Asn Val Phe Lys Ala Asn Asp Ile Val Val
370                 375                 380

Ala Leu Leu Gln Glu Lys Gly Ala Leu Leu His Val Glu Lys Met Gln
385                 390                 395                 400

His Ser Tyr Pro Cys Cys Trp Arg His Lys Thr Pro Ile Ile Phe Arg
                405                 410                 415

Ala Thr Pro Gln Trp Phe Val Ser Met Asp Gln Lys Gly Leu Arg Ala
            420                 425                 430

Gln Ser Leu Lys Glu Ile Lys Gly Val Gln Trp Ile Pro Asp Trp Gly
        435                 440                 445

Gln Ala Arg Ile Glu Ser Met Val Ala Asn Arg Pro Asp Trp Cys Ile
450                 455                 460

Ser Arg Gln Arg Thr Trp Gly Val Pro Met Ser Leu Phe Val His Lys
465                 470                 475                 480

Asp Thr Glu Glu Leu His Pro Arg Thr Leu Glu Leu Met Glu Glu Val
                485                 490                 495

Ala Lys Arg Val Glu Val Asp Gly Ile Gln Ala Trp Trp Asp Leu Asp
            500                 505                 510

Ala Lys Glu Ile Leu Gly Asp Glu Ala Asp Gln Tyr Val Lys Val Pro
        515                 520                 525

Asp Thr Leu Asp Val Trp Phe Asp Ser Gly Ser Thr His Ser Ser Val
530                 535                 540

Val Asp Val Arg Pro Glu Phe Ala Gly His Ala Ala Asp Met Tyr Leu
545                 550                 555                 560

Glu Gly Ser Asp Gln His Arg Gly Trp Phe Met Ser Ser Leu Met Ile
                565                 570                 575

Ser Thr Ala Met Lys Gly Lys Ala Pro Tyr Arg Gln Val Leu Thr His
            580                 585                 590

Gly Phe Thr Val Asp Gly Gln Gly Arg Lys Met Ser Lys Ser Ile Gly
        595                 600                 605

Asn Thr Val Ser Pro Gln Asp Val Met Asn Lys Leu Gly Ala Asp Ile
610                 615                 620

Leu Arg Leu Trp Val Ala Ser Thr Asp Tyr Thr Gly Glu Met Ala Val
625                 630                 635                 640

Ser Asp Glu Ile Leu Lys Arg Ala Ala Asp Ser Tyr Arg Arg Ile Arg
                645                 650                 655

Asn Thr Ala Arg Phe Leu Leu Ala Asn Leu Asn Gly Phe Asp Pro Ala
            660                 665                 670

Lys Asp Met Val Lys Pro Glu Glu Met Val Val Leu Asp Arg Trp Ala
        675                 680                 685
```

-continued

```
Val Gly Cys Ala Lys Ala Ala Gln Glu Asp Ile Leu Lys Ala Tyr Glu
    690             695             700

Ala Tyr Asp Phe His Glu Val Val Gln Arg Leu Met Arg Phe Cys Ser
705             710             715             720

Val Glu Met Val Ser Phe Tyr Leu Asp Ile Ile Lys Asp Arg Gln Tyr
            725             730             735

Thr Pro Lys Arg Thr Val Trp Ala Arg Arg Ser Cys Gln Thr Ala Leu
            740             745             750

Tyr His Ile Ala Glu Ala Leu Val Arg Trp Met Ala Pro Ile Leu Ser
            755             760             765

Phe Thr Ala Asp Glu Val Trp Gly Tyr Leu Pro Gly Glu Arg Glu Lys
        770             775             780

Tyr Val Phe Thr Gly Glu Trp Tyr Glu Gly Leu Phe Gly Leu Ala Asp
785             790             795             800

Ser Glu Ala Met Asn Asp Ala Phe Trp Asp Glu Leu Leu Lys Val Arg
                805             810             815

Gly Glu Val Asn Lys Val Ile Glu Gln Ala Arg Ala Asp Lys Lys Val
                820             825             830

Gly Gly Ser Leu Glu Ala Ala Val Thr Leu Tyr Ala Glu Pro Glu Leu
            835             840             845

Ser Ala Lys Leu Thr Ala Leu Gly Asp Glu Leu Arg Phe Val Leu Leu
    850             855             860

Thr Ser Arg Arg Tyr Val Ala Asp Tyr Asn Asp Ala Pro Ala Asp Ala
865             870             875             880

Gln Gln Ser Glu Val Leu Lys Gly Leu Lys Val Ala Leu Ser Lys Ala
            885             890             895

Glu Gly Glu Lys Cys Pro Arg Cys Trp His Tyr Thr Gln Asp Val Gly
            900             905             910

Lys Val Ala Glu His Ala Glu Ile Cys Gly Arg Cys Val Ser Asn Val
            915             920             925

Ala Gly Asp Gly Glu Lys Arg Lys Phe Ala
    930             935
```

ASSAY FOR DETECTING INHIBITORS OF AMINOACYL-TRNA SYNTHETASES

This application is a continuation of application Ser. No. 08/320,473, filed Oct. 6, 1994, now abandoned.

The present invention relates to a new assay procedure for detecting compounds which inhibit the activity of certain aminoacyl-tRNA synthetases, to the use of these procedures for identifying compounds which have such activity for use as antibiotics or herbicides, to herbicides derived thereby, and to a novel cDNA sequence encoding *E. coli* isoleucyl-tRNA synthetase.

Aminoacyl-tRNA synthetases are enzymes found in all bacteria, plants and animals and are required to make protein. Inhibitors of the bacterial enzymes are potentially useful as antibiotics and the applicants have discovered that they may also have application as herbicides.

It is vital that the genetic code is accurately translated into protein. To ensure that this happens each aminoacyl-tRNA synthetase must attach the right (cognate) amino acid to the right (cognate) species of tRNA. To ensure that this happens, certain of these enzymes have evolved "editing" mechanisms to hydrolyse (at different stages) inappropriate intermediates complexes and "mischarged" tRNA species. Particular examples are valine, a non-cognate amino acid with respect to isoleucyl-tRNA synthetase (hereinafter referred to as ITRS) (1), threonine (2), a non-cognate amino acid with respect to valyl-tRNA synthetase and homocysteine, a non-cognate amino acid with respect to methionyl-tRNA synthetase.

The applicants have found a means of using these editing mechanisms to develop an assay technique for discovering inhibitors of enzyme activity and consequently of biologically active compounds having industrial applicability.

According to one aspect of the present invention there is provided an assay for detecting inhibitors of an aminoacyl-tRNA synthetase, which when reacted with a divalent metal cation, a corresponding species of tRNA and an appropriate non-cognate amino acid, will result in the hydrolysis of ATP to pyrophosphate; the assay comprising incubating the said divalent metal cation, ATP, the said tRNA, the said non-cognate amino acid, inorganic pyrophosphatase and the said aminoacyl-tRNA synthetase, in at least a partially pure form, both with and without a potential inhibitor and providing detecting means for phosphate and comparing the results obtained.

According to another aspect of the present invention there is provided an assay for detecting an inhibitor of isoleucyl-tRNA synthetase of *E. coli* comprising (a) incubating magnesium ions, adenosine triphosphate (ATP), a corresponding species of tRNA, isoleucyl-tRNA synthetase and inorganic pyrophosphatase with valine; (b) simultaneously incubating a similar mixture further containing a potential inhibitor of the enzyme; (c) detecting phosphate production from the incubates; and (d) comparing the results.

As used herein, the expression "partially pure" used in relation to enzyme means that the enzyme preparation is substantially free of interfering activities, in particular is substantially free of phosphatases and, for example, in the particular case of the assay for ITRS exemplified, free of valyl-tRNA synthetase.

The tRNA employed in the assay technique may be pure tRNA appropriate for the particular enzyme or a mixture of tRNAs, such as the mixture of tRNA species from *E. coli* strain W commercially obtainable from Sigma (UK) Ltd, provided that the mixture contains sufficient of the tRNA appropriate for the particular enzyme.

The assay of the invention is applicable for the screening of chemicals for biological activity in a commercial environment. Consequently the term "readily hydrolysable" means that the assay reaction can proceed at a useful rate.

Particular examples of enzymes and amino acids which can be employed in this screen because of the editing mechanism by which the misacylated products are removed are ITRS, valyl-tRNA synthetase and methionyl-tRNA synthetase with valine, threonine and homocysteine respectively.

The divalent metal cation is preferably magnesium or manganese. Magnesium is especially preferred.

In a preferred embodiment the enzyme employed in the assay is ITRS from a bacterial source, preferably *E. coli*, and the amino acid is valine.

The assay is based upon the principles exemplified below. The two partial reactions of ITRS (enzyme) involved in the biosynthesis of the aminoacyl-tRNA can be represented as follows:

1) Enzyme (ITRS)+ATP+ile⇌Enzyme:ile-AMP+PPi 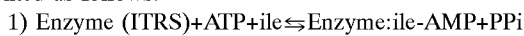

ITRS, in the presence of $Mg^{2+}$ ions catalyses a partial reaction in which pyrophosphate (PPi) is released and an aminoacyl adenylate (ile-AMP) is formed which remains very tightly bound to the enzyme.

2) Enzyme:ile-AMP+tRNA$^{ile}$⇌ile-tRNA$^{ile}$+AMP+Enzyme  The enzyme-bound aminoacyl adenylate reacts with the cognate tRNA to transfer the ile to the tRNA and to release adenosine monophosphate (AMP).

As can be seen, pyrophosphate is produced in step 1. Adding inorganic pyrophosphatase converts this to phosphate (which can be measured, for example, colormetrically by a suitable phosphate determination method such as that involving malachite green described by Lanzetta et al (3) and slightly modified by Howard and Ridley (4)). Consequently it should be possible to detect ITRS activity by detecting phosphate.

However, the above two reactions are tightly coupled. The stoichiometry requires one equivalent of tRNA to react for each pyrophosphate released. Large amounts of tRNA would be needed to generate enough pyrophosphate and subsequently phosphate to detect. This would be too costly to employ on a routine basis and for use in a high throughout screen.

When valine is substituted for isoleucine it also initially reacts to form the aminoacyl AMP bound to the enzyme. The reaction scheme can be represented as follows:

1. Enzyme+ATP+val⇌Enzyme: val-AMP+PPi 
2. tRNA$^{ile}$+Enzyme: val-AMP⇌tRNA$^{ile}$+Enzyme+val+AMP 

In this case rather than forming the aminoacyl-tRNA, it is rapidly hydrolysed by the ITRS enzyme in the presence of tRNA$^{ile}$ (5). The assay of the invention makes use of this in that valine allows the tRNA to be recycled so that it does not limit the extent of the reaction. Thus, the enzyme catalyses the hydrolysis of ATP to PPi (and, via pyrophosphatase, ultimately, Pi).

Since the enzyme catalyses the hydrolysis of the non-cognate aminoacyl adenylate bound to the enzyme and there is no transfer to the tRNA, only catalytic amounts of tRNA are required. In addition the starting enzyme and valine are also regenerated while generating pyrophosphate.

Experiments with the assay conditions have shown that once the reaction with the ITRS enzyme was started, a linear rate could be maintained for at least 40 minutes. A colour change of >0.3 OD units is preferred.

The amount of tRNA which is employed in the reaction is generally low since the tRNA is recycled in the reaction. For example, doses of from about 0.05 mg to about 0.3 mg/200 µl reaction mixture may be employed. As discussed above, this may be pure or mixed tRNA species from E. coli.

In one preferred embodiment, mixed tRNA species from E. coli from Sigma (UK) Ltd is added in an amount of about 0.1mg/200 µl reaction mixture.

The amount of ATP present can be from about 0.05 to about 10 mM.

The Km for valine is about 0.5 mM, so at least 0.5 mM of valine, suitably from about 0.5 mM to about 25 mM of valine, preferably about 5 mM valine is used to obtain near maximum rates. In contrast, the Km for Ile using an $^3$H-Ile assay was found to be about 4.3 µM.

Purified or partially purified enzyme may be prepared by conventional techniques (6) including use of recombinant DNA technology. Using ITRS obtained from E. coli, and partially purified as described below, amounts of from about 0.10 µg to about 5 µg are suitably employed. Based on this amount, suitable assay times have been found to be up to about 90 minutes or longer.

We have also now sequenced the gene encoding for E. coli ITRS. Thus, according to another aspect of the present invention there is provided a cDNA sequence as shown in Seq ID No 1, including non-critical allelic variations of that sequence.

According to yet another aspect of the present invention there is provided an amino acid sequence as shown in Seq ID No 2, including variants thereof having non-critical amino acid substitution(s) or deletion(s) at one or more locations in that sequence.

The present invention includes sequences having at least 70% nucleic acid homology with the sequence shown in Seq ID No 1, and which encode for functionally equivalent proteins. In a preferred embodiment, the nucleic acid sequence has at least 75%, 80%, 85%, 90%, 95%, 97% or 99% homology with the sequence shown in Seq ID No 1.

The present invention includes functionally equivalent sequences to that shown in Seq ID No 2, having at least 70% homology with said sequence. In a preferred embodiment, the amino acid sequence has at least 75%, 80%, 85%, 90%, 95%, 97% or 99% homology with the sequence shown in ID Seq No 2.

It will be appreciated that the expressed ITRS can be used in the assay of the present invention.

By using the assay technique described above, it is possible to carry out high throughput screens for detecting inhibitors of the enzymes. In a further aspect of the invention there is provided an enzyme inhibitor having biological application detected by an assay method as described above.

In particular the applicants have found that inhibitors of ITRS may have application as herbicides. Such compounds are described in our co-pending International Patent Publication No. WO93/19599.

In yet a further aspect of the invention there is provided a herbicidal compound which acts by inhibiting the plant isoleucyl-tRNA synthetase enzyme excluding those compounds of International Patent Publication No. WO93/19599 of general formula (I) or (IA) or (IB) where Y represents a group of sub-formula (IC) or (ID or (IE) and wherein $R^2$ is a group CO-XR$^3$ wherein X is O or S and $R^3$ is hydrogen or an agrochemically acceptable ester-forming radical; or $R^2$ is a group —R$^4$ wherein R$^4$ is an optionally substituted aryl or heterocyclic group; or $R^2$ is a group CO—NR$^5$R$^6$ wherein R$^5$ and R$^6$ are the same or different and each represent an agrochemically acceptable amide-forming radical; stereoisomers of the compounds of formula (I), (IA) and (IB) and salts of the compound of formula (I), (IA) and (IB) wherein $R^2$ is COXR$^3$, X is O and $R^3$ is hydrogen.

The following examples illustrate the invention.

1. Partial Purification of E. coli ITRS a) Cell breakage 100 g of E. coli cell paste was mixed with 200 ml of buffer A (100 mM Tris (tris(hydroxymethyl)aminomethane) pH 7.4, 30 mM KCl, 0.5 mM MgCl$_2$, 0.1 mM EDTA (ethylenedinitrilotetraacetate), 4 mM 2-mercaptoethanol, 6 mM DTT (dithiothreitol) and 1 mM benzamidine). The cells were broken in a French press at 8,000 psi (5.5×10$^4$ kPa). The extract was spun at 23,500×g (12,000 rpm) in a 6×250 ml Sorvall GSA rotor for 20 minutes at 4° C.

b) Precipitation

The supernatant was removed and 2.5% protamine sulphate in buffer A was added in a dropwise manner to a final concentration of 0.1%. The extract was centrifuged at 23,500×g (12,000 rpm) for 20 minutes. The supernatant was removed, and 50% ammonium sulphate added slowly and left to mix on ice for 30 minutes. The extract was spun again at 12,000 rpm for 15 minutes to form a pellet.

c) Gel filtration on a Sephadex G-50 column

The pellet was resuspended in a small amount of buffer B (25 mM Tris pH 7.4, 5 mM MgCl$_2$, 1 mM EDTA, 4 mM 2-mercaptoethanol). A further spin in a 8×50 ml Sorvall SS-34 rotor at 39,000×g (18,000 rpm) for 15 minutes was carried out prior to the extract being added to a Sephadex G-50 column (5 cm i.d.) with a bed volume of 250 ml. The protein eluted with buffer B was collected and stored at −80° C.

d) Ion-exchange on a Q-Sepharose Column

A pre-equilibrated Pharmacia Q-Sepharose column (11.5 cm×5 cm) in buffer B was prepared. The extract from the Sephadex G-50 column was added, and a 0 to 1M NaCl gradient applied. All the fractions from this column were kept and analysed by the radiolabelled method described below. The active fractions (47–57) were pooled, and had 90% ammonium sulphate added and were then spun at 12,000×g (17,400 rpm) in the 8×50 ml Sorvall SS-34 rotor for 15 minutes. The supernatant was removed and the resulting pellet was dissolved in buffer B.

e) Gel Filtration on a Superdex-200 Column

Five ml of the extract from step d) was added to a pre-packed Pharmacia Superdex-200 HiLoad column (2 cm i.d.) with a bed volume of 120 ml. It was pre-equilibrated in buffer B and 50 mM NaCl. All of the fractions were kept separate and tested using the radiolabelled assay. Fractions 25–40 were pooled and an equal volume of glycerol was added. When this extract was used for the initial development work on the colorimetric assay it was found to contain contaminating phosphatase activity.

f) Removal of Contaminating Phosphatase Activity

Using a high resolution Q-Sepharose column with a gradient of 0–1M NaCl on an FPLC system, fractions containing ITRS activity free of contaminating phosphatase were eluted at 0.3M NaCl.

2. Measurement of ITRS Activity using a $^3$H-Isoleucine-Based Radiolabelled Assay The activity of ITRS during fractionation was monitored using conditions based on the method described by Steinmetz and Weil (7), and as described below. Stock reagents used in the method are as follows:

Buffer solution 500 mM Tris-HCl pH 7.4, 150 mM MgCl$_2$, 6H$_2$O, 300 mM KCl, 25 mM glutathione, and 1% bovine serum albumin (BSA).

ATP 10 mM in 50 mM-Tris-HCl pH 7.4.

tRNA (mixed)

Approximately 0.54 nmoles tRNA$^{ile}$/mg from the *E. coli* strain W (supplied by Sigma (UK) Ltd). A stock was made of 50 mg mixed tRNA/ml 50 mM Tris-HCl pH 7.4.
Isoleucine L-[4,5-$^3$H]-Isoleucine (obtained from Amersham) at approximately 100 Ci/mmole in 2% aqueous ethanol. A 100 μM stock was prepared of 50 μl $^3$H-isoleucine, 100 μl cold isoleucine, and 850 μl 50 mM Tris-HCl pH 7.4.
Enzyme—ITRS Prepared as described above. The specific activity of the enzyme used in the present example was approximately 145 nM of product formed/minute/mg, and was about 5%–10% active. The enzyme was diluted as appropriate. It will be appreciated that the enzyme amounts in the assay can be adjusted according to the purity of the enzyme used.

The assay mixture for a final volume of 200 μl was composed of:

20 μl buffer solution
20 μl ATP
20 μl tRNA
20 μl $^3$H-Isoleucine solution
100 μl 50 mM Tris-HCl pH 7.4

The standard assay (in 200 μl) was carried out in quadruplicate in Eppendorf microcentrifuge tubes. The ingredients were preincubated for 2–3 minutes at 37° C., and the reaction started by addition of approximately 20 μl of the appropriately diluted enzyme extract as described above.

The final reaction contained reagents in the following concentrations:

50 mM Tris-HCl, pH 7.4
15 mM MgCl$_2$, 6H$_2$O
30 mM KCl
2.5 mM Glutathione
0.1% bovine serum albumin
1 mM ATP
5 mg ml$^{-1}$ tRNA
10 μM Isoleucine containing $^3$H-Ile The assay was incubated at 37° C. for 20 minutes, and stopped by addition of 50 μl 20% TCA, and the tubes placed on ice.

200 μl of the reaction mixture was pipetted onto 1.5 cm$^2$ cellulose 3MM filters. The filters were washed (in groups of 4) as follows: 1×10% TCA, 2×5% TCA, and 2×ethanol using fresh wash medium for each set of replicates to avoid cross contamination. The dried filters were placed in 20 ml scintillation vials and the radioactivity counted in 15 ml Optiphase.

2. Measurement of ITRS activity using a Colorimetric Assay based on using Valine as Substrate Incubations were set up in quadruplicate (as above) with a final volume of 200 μl as described below. Stock reagents used in the method were as follows:
Buffer solution 500 mM Tris-HCl pH 7.4, 150 mM MgCl$_2$, 6H$_2$O, 300 mM KCl, 25 mM glutathione, and 1% bovine serum albumin (BSA).
ATP 7.5 mM in 50 mM Tris-HCl pH 7.4.
tRNA (mixed)

Approximately 0.54 nmoles TRNA$^{ile}$/mg from the *E. coli* strain W (supplied by Sigma (UK) Ltd). A stock was made of 1.2 mg mixed tRNA/ml 50 mM Tris-HCl pH 7.4.
L-Valine A 30 mM stock in 50 mM Tris-HCl pH 7.4.
Inorganic Pyrophosphatase This was in the form of the HPLC purified grade from Bakers yeast supplied by Sigma (UK) Ltd as a lyophilized powder. This was made up in 50 mM Tris-HCl pH 7.4 to a concentration of 10 units/ml.
Enzyme—ITRS Prepared as described above. The specific activity of the enzyme used in the present example was approximately 145 nM of product formed/minute/mg, and was about 5%–10% active. The enzyme was diluted as appropriate. It will be appreciated that the enzyme amounts in the assay can be adjusted according to the purity of the enzyme used.

The assay mixture for a final volume of 200 μl was composed of:

20 μl buffer solution
20 μl ATP
20 μl tRNA
20 μl inorganic pyrophosphatase
100 μl L valine The standard assay (in 200 μl) was carried out in quadruplicate in Eppendorf microcentrifuge tubes. The ingredients were pre-incubated for 2–3 minutes at 37° C. and the reaction started by addition of 20 μl of appropriately diluted enzyme extract (as described above).

Thus the final reaction contained reagents in the following concentrations:

50 mM Tris-HCl pH 7.4
10 mM MgCl$_2$
30 mM KCl
2.5 mM Glutathione
0.75 mM ATP
15 mM Valine
0.12 mg of mixed tRNA species from *E. coli* (as described above) HPLC purified from Bakers yeast available from by Sigma (UK) Ltd 1 unit/μl of inorganic pyrophosphatase and
an appropriate concentration of ITRS (for example 1–2 g/ml of the enzyme as described above).

The samples were incubated at 37° C. for 20–60 minutes. The reaction is stopped by the addition of a Malachite Green containing reagent as described by Howard and Ridley (4) and subsequently quenched with the addition of 34% citric acid. The optical absorbance is then measured at a wavelength of 630 nm using a spectrophotometer. The Km value of 0.048 mM of ATP was determined using the novel calorimetric assay was in close agreement with the Km of 0.047 mM obtained using the $^3$H-Ile assay.

The inhibition constants of two compounds were measured and the results compared with the values obtained using the standard $^3$H-isoleucine assay. Compound 1 was tested at 0, 0.25 μM and 1.0 μM concentrations with varying $^3$H-Isoleucine concentrations up to 100 μM, and was seen to be competitive with respect to isoleucine.

Results

Concentration giving 50% inhibition (I$_{50}$) measured using the valine-based assay of the present invention:

|  | Compound 1 | Compound 2 |
| --- | --- | --- |
| I$_{50}$ | 2000 nM | 38 nM |

Concentration giving 50% inhibition (I$_{50}$) measured using the standard $^3$H-isoleucine radiometric assay:

|     | Compound 1 | Compound 2 |
| --- | --- | --- |
| $I_{50}$ | 109 nM | 2.3 nM |

The two assays both detected the compounds as inhibitors and both assays indicated that the potencies of the two inhibitors were different. The actual values are different because:

1) Compound 2 is, in reality, more potent than can be measured and the apparent $I_{50}$ value is mainly determined by the concentration of enzyme in the assay (8). Since the radiometric assay is more sensitive it uses less enzyme and therefore yields a lower apparent $I_{50}$ value than in the assay of the present invention.

2) Both compound 1 and compound 2 are competitive with the amino acid. In the case of the radiometric assay, the amino acid, isoleucine, is used at a concentration only approximately 2 fold above the Km whereas in the assay of the present invention it is some 30 fold greater. Thus, allowing for this fifteen fold difference in the ratio of amino acid concentration to Km, the two values given by the two assays are in good agreement. It will therefore be appreciated that the valine-based assay described here is useful as a calorimetric method for detecting inhibitors of *E. coli* ITRS.

3. Sequencing of the *E. coli* ITRS gene

The gene was sequenced in two stages:

a) The Promega "Erase-A-Base" kit (Promega Cat. No. E5850) was used. The gene was cloned into the vector pGEM3Zf(−). The Erase-A-Base system allows the construction of a series of unidirectional nested deletion sets from plasmid or M13 clones using the procedure developed by Henikoff (9). In this case the deletion mutants, each containing a different part of the gene, were sequenced with the pUC/M13 reverse sequence primer (5'-AACAGCTATGACCATG-3') using the Sequenase Version 2.0 kit.

b) About 60% of the gene was sequenced using the "Erase-A-Base" system. This sequence information was used to design synthetic oligonucleotide primers (listed below) so that the gaps in the gene sequence could be read. The gaps were filled in and the entire coding nucleotide sequence of the gene obtained.

Primers for top strand

ITS39F: 5'-GGCATCATCCGTGCGGCT-3'
ITS91F: 5'-TATGTGCCTGGCTGGGAC-3'
ITS114F: 5'-GGTGAGAAATTCACCGCC-3'
ITS226F: 5'-TTTGCCGTAAGCAACGTT-3'
ITS346F: 5'-GGTCAGAAATACGGCCTG-3'
ITS393F: 5'-CTGCTGCACGTTGAGAAA-3'
ITS566F: 5'-CAACACCGCGGCTGGTTC-3'
ITS765F: 5'-GCACCAATCCTCTCCTTC-3'
ITS808F: 5'-TTCTGGGACGAGCTGTTG-3'

Primers for bottom strand

ITS252R: 5'-TTGCGCGGTTGGCAGGCA-3'
ITS336R: 5'-CGCGGTGTGAACGGCACC-3'
ITS526R: 5'-TTTCACGTACTGATCAGC-3'

References (1) Fersht et al (1977) Biochemistry, 16, 1025–1028,
(2) Fersht et al (1976) Biochemistry, 15, 3342–3346,
(3) Lanzetta et al (1979) Anal. Biochem., 100, 95–97,
(4) Howard and Ridley (1990) FEBS. Lett., 261, 261–264,
(5) Baldwin, A. N. and Berg, P. (1966) J. Biol. Chem., 241, 839–845
(6) Durekovic, A., Flossdorf, J and Kula, M. R. (1973) Eur. J. Biochem, 36, 528–533,
(7) Steinmetz, A. and Weil, J-H. (1986) Methods in Enzymology, 118, 212–231
(8) Henderson (1973) Biochem. J., 135, 101–107,
(9) Henikoff, S. (1984) Gene, 28, 351

CHEMICAL FORMULAE
(IN DESCRIPTION)

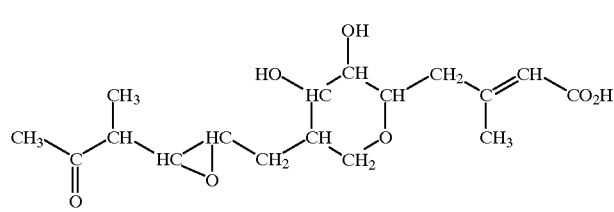

1

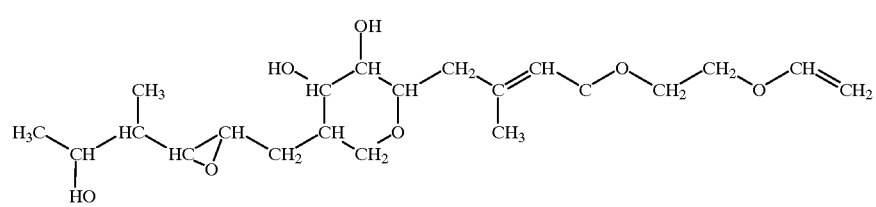

2

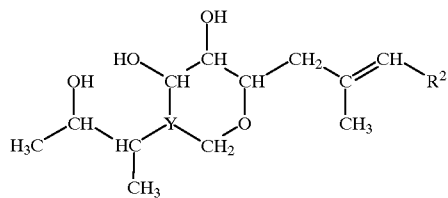
(I)
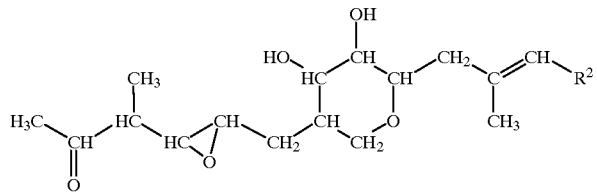
(IA)
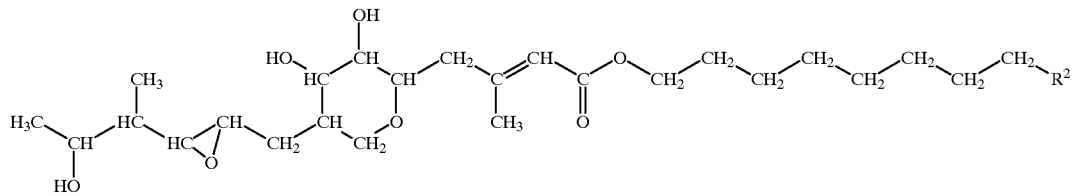
(IB)
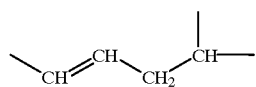
(IC)
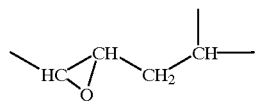
(ID)
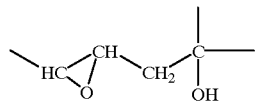
(IE)

I claim:
1. A method of identifying a compound which is an inhibitor of an aminoacyl-tRNA synthetase comprising the steps of
   a) incubating a mixture comprising a divalent metal cation, adenosine triphosphate, an aminoacyl-tRNA synthetase in at least partially pure form, cognate RNA, a non-cognate amino acid and inorganic pyrophosphatase, wherein phosphate anion is produced in said mixture;
   b) incubating a potential inhibitor compound with a mixture comprising a divalent metal cation, adenosine triphosphate, an aminoacyl-tRNA synthetase in at least partially pure form, cognate tRNA, a non-cognate amino acid and inorganic pyrophosphatase, wherein phosphate anion is produced in said mixture;
   c) determining the amount of phosphate anion produced in step a) and step b); and
   d) comparing the amount of phosphate anion produced in step a) with the amount of phosphate anion produced in step b), wherein a smaller amount of phosphate anion determined for step b) in comparison with step a) indicates that said potential inhibitor compound inhibits said aminoacyl-tRNA synthetase and is an inhibitor of said aminoacyl-tRNA synthetase.

2. The method of claim 1 wherein said aminoacyl-tRNA synthetase is isoleucyl-tRNA, valyl-tRNA synthetase or methionyl-tRNA synthetase and said non-cognate amino acid is valine, threonine or homocysteine, respectively.

3. The method of claim 1 wherein said phosphate anion is determined colorimetrically.

4. The method of claim 1 wherein said method is operated as a high throughput screening method.

5. A method of identifying a compound which is an inhibitor of isoleucyl-tRNA synthetase comprising the steps of
   a) incubating a mixture comprising magnesium ions, adenosine triphosphate, isoleucyl-tRNA synthetase, cognate tRNA, valine and inorganic pyrophosphatase wherein phosphate anion is produced in said mixture;
   b) incubating a potential inhibitor compound with a mixture comprising magnesium ions, adenosine triphosphate, isoleucyl-tRNA synthetase, cognate tRNA, valine and inorganic pyrophosphatase wherein phosphate anion is produced in said mixture;
   c) determining the amount of phosphate anion produced in step a) and step b);
   d) comparing the amount of phosphate anion produced in step a) with the amount of phosphate anion produced in step b) wherein a smaller amount of phosphate anion determined for step b) in comparison with step a) indicates that said potential inhibitor compound inhibits said isoleucyl-tRNA synthetase and is an inhibitor of said isoleucyl-tRNA synthetase.

6. The method of claim 5 wherein said phosphate anion is determined colorimetrically.

7. The method of claim 5 wherein said method is operated as a high throughput screening method.

* * * * *